US008777168B2

(12) United States Patent
Hassid (10) Patent No.: US 8,777,168 B2
(45) Date of Patent: Jul. 15, 2014

(54) SUPPORT STRUCTURE FOR PROTECTIVE WEAR (76) Inventor: Babak Hassid, New York, NY (US)

(*) Notice: Subject to any disclaimer, the term of this patent is extended or adjusted under 35 U.S.C. 154(b) by 0 days.

(21) Appl. No.: 13/045,469

(22) Filed: Mar. 10, 2011

(65) Prior Publication Data

US 2012/0228439 A1 Sep. 13, 2012

(51) Int. Cl.
A61B 6/10 (2006.01)
A47G 25/90 (2006.01)
A47G 25/06 (2006.01)
A61B 19/00 (2006.01)
A47F 7/19 (2006.01)

(52) U.S. Cl.
CPC ............. *A47G 25/0671* (2013.01); *A61B 19/26* (2013.01); *A47G 25/90* (2013.01); *A47F 7/19* (2013.01)
USPC ...................... 248/125.8; 250/516.1; 211/85.3

(58) Field of Classification Search
CPC ............... G21F 3/00; G21F 3/02; A47F 7/24; A47F 8/02; A61B 6/10; A41H 5/01
USPC .............. 248/125.1, 127, 157, 161, 121, 126, 248/125.8, 188.5, 339; 250/516.1, 515.1; 211/85.3, 196; 223/89
See application file for complete search history.

(56) References Cited

U.S. PATENT DOCUMENTS

| 984,591 | A | * | 2/1911 | Nelson | 211/196 |
| 1,636,419 | A | * | 7/1927 | Hollander | 250/519.1 |
| 1,959,977 | A | * | 5/1934 | Elvin | 223/68 |
| 2,413,221 | A | * | 12/1946 | Elston | 223/89 |
| 2,654,484 | A | * | 10/1953 | Win et al. | 211/1.3 |
| 2,747,824 | A | * | 5/1956 | Darnell, Jr. | 248/412 |
| 3,256,440 | A | * | 6/1966 | Stark | 250/516.1 |
| 3,447,488 | A | * | 6/1969 | David | 108/28 |
| 4,351,441 | A | * | 9/1982 | Schramm | 211/207 |
| 4,548,328 | A | * | 10/1985 | Brauning | 211/205 |
| D301,094 | S | * | 5/1989 | Muxlow | D6/411 |
| 5,015,864 | A | * | 5/1991 | Maleki | 250/516.1 |
| 5,220,175 | A | * | 6/1993 | Cole | 250/515.1 |
| 5,421,548 | A | * | 6/1995 | Bennett et al. | 248/129 |
| 6,170,679 | B1 | * | 1/2001 | Frye et al. | 211/113 |
| 6,213,434 | B1 | * | 4/2001 | Reichanadter, Jr. | 248/125.8 |
| 6,726,033 | B2 | * | 4/2004 | Sparkowski et al. | 211/85.3 |
| 6,749,073 | B2 | * | 6/2004 | McNab | 211/85.3 |
| 6,796,446 | B2 | * | 9/2004 | Segall et al. | 211/206 |
| 7,631,773 | B1 | * | 12/2009 | Calabrisotto et al. | 211/196 |
| 7,896,298 | B2 | * | 3/2011 | Meyers et al. | 248/125.8 |
| 8,207,516 | B2 | * | 6/2012 | Rees | 250/516.1 |

(Continued)

FOREIGN PATENT DOCUMENTS

| DE | 9108486 U1 * | 9/1991 | |
| DE | 202013104967 U1 * | 11/2013 | |
| FR | 2669816 A3 * | 6/1992 | A47F 7/19 |
| GB | 2469259 A * | 10/2010 | A47F 5/13 |

*Primary Examiner* — Terrell McKinnon
*Assistant Examiner* — Eret McNichols
(74) *Attorney, Agent, or Firm* — Marger, Johnson & McCollom, P.C.

(57) ABSTRACT

A support apparatus has a base having at least one portion positioned to rest on a solid surface, at least one vertical support extending upwards from the base, the vertical support having a lower fixed portion and an upper adjustable portion, at least one horizontal support extending outwards from the vertical support, the horizontal support positioned to be insertable into a protective garment while being worn by a user.

8 Claims, 10 Drawing Sheets (56) References Cited

U.S. PATENT DOCUMENTS

| | | | |
|---|---|---|---|
| 2005/0011847 A1* | 1/2005 | Goodwin | 211/196 |
| 2005/0082244 A1* | 4/2005 | Ho | 211/85.23 |
| 2007/0221796 A1* | 9/2007 | Silverman et al. | 248/161 |
| 2010/0059463 A1* | 3/2010 | Sun | 211/85.3 |
| 2010/0270247 A1* | 10/2010 | Durham | 211/85.3 |
| 2011/0006180 A1* | 1/2011 | Newkirk et al. | 248/219.1 |
| 2011/0174997 A1 | 7/2011 | Rees | |
| 2013/0270462 A1* | 10/2013 | Beck | 250/516.1 |

* cited by examiner

SUPPORT STRUCTURE FOR PROTECTIVE WEAR

BACKGROUND

Medical practitioners, such as interventional cardiologists and neurosurgeons, may use x-ray images during procedures in operating rooms. The environment prevents the practitioners from standing behind protective barriers that shield them from the radiation. Many wear some sort of protective lead apron such as those manufactured by AADCO Medical, Inc. in their line of Ray Shield® aprons and vests.

The protective wear contains lead or other metals to absorb the x-ray radiation, making the protective garments relatively heavy compared to standard surgical garments. Many practitioners may have to wear these heavy garments for long hours during complicated procedures, or on days when they have several procedures schedules. As a result, practitioners may suffer shoulder, back and hip pain on a daily basis and over time may suffer permanent damage.

One solution is to make the garments lighter by using thinner layers of metals, or mixing the metals with other materials. This affects the protection level afforded by the garments, and the overall reduction of the weight of the garment is relatively small. One product line announces a reduction in weight of 30%, reducing the weight from 10.5 pounds to 7.5 pounds. While this may help in the short term, the practitioner is still carrying several pounds of gear every day.

Another solution is to make the apron removable as soon as the portion of the procedure that uses x-rays is no longer needed. However, for many procedures, x-rays are used most of the time. Further, the removable apron requires a pause in the procedure while another person loosens the fasteners from the protective gear so as to not interfere with the sterility of the practitioner's gloves.

However, these solutions still involve the practitioner having to carry the weight of the protective gear for long periods of time.

DETAILED DESCRIPTION OF THE EMBODIMENTS

Figure 1:
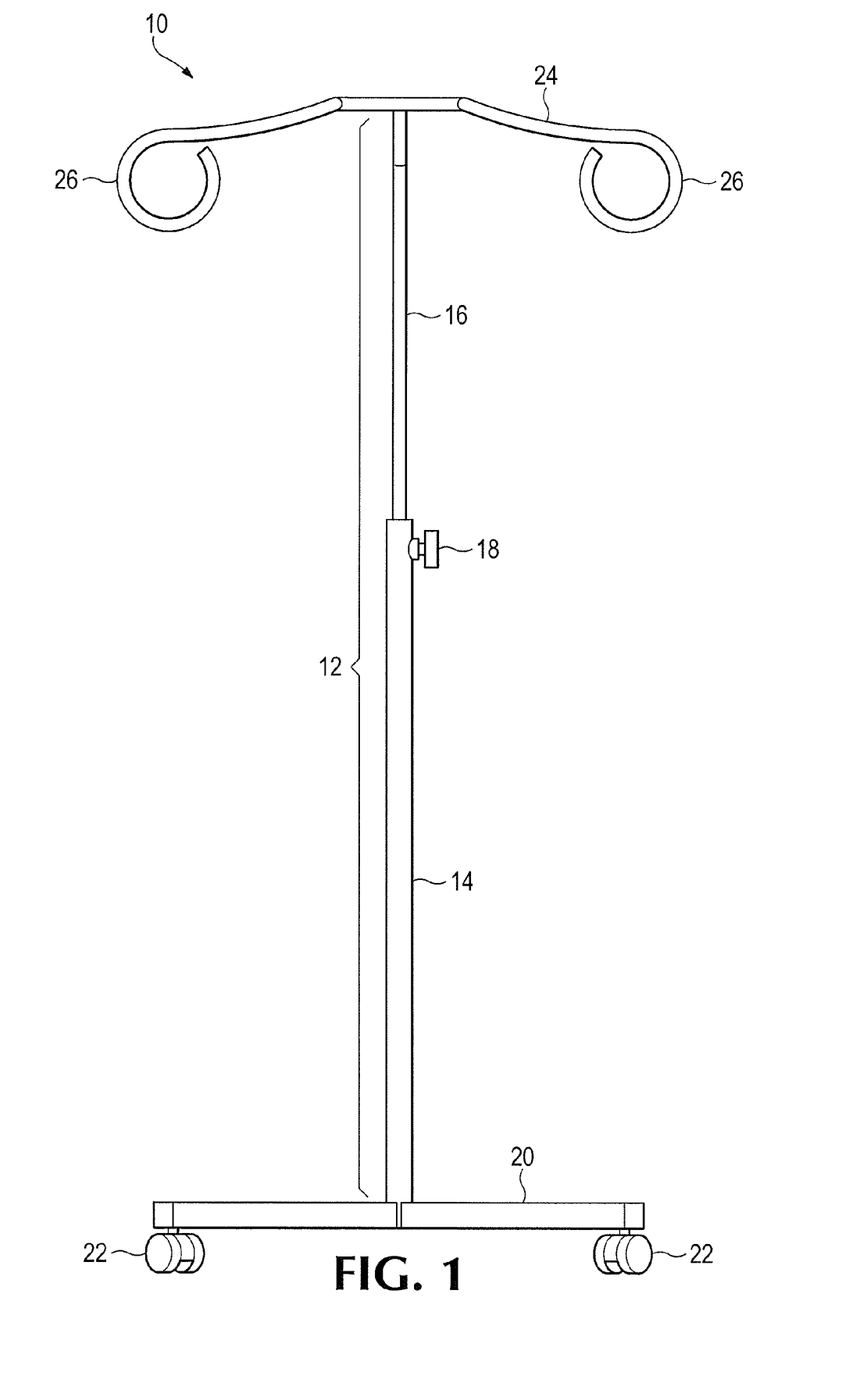
FIG. 1 shows an embodiment of a support structure for protective wear.

FIG. 1 shows an embodiment of a support apparatus for protective wear. For ease of understanding, and with no intention of limiting the scope of the claims, one could imagine the practitioner/user standing in front of the apparatus 10 shown in FIG. 1, with the apparatus essentially behind the practitioner. The apparatus would support the protective wear while the practitioner was wearing it. This affords full protection from radiation while taking the weight of the garment off of the practitioner.

Many different types of practitioners use radiation protection, including but not limited to, interventional cardiologists and neurosurgeons, cardiac electrophysiologists, gastroenterologists, orthopedic surgeons, vascular surgeons, etc. Hip and back pain has become common among these practitioners because of long hours standing and bending over procedure tables wearing the protective wear.

As shown in FIG. 1, the apparatus 10 has a vertical support 12 that has a lower fixed portion 14 and an upper fixed portion 16. This allows the height of the horizontal supports to be changed to suit the height of the practitioner. The adjustable portion may have an adjustment control to fix the adjustable portion in place. Alternatively, the adjustable portion may remain at a particular height because of the height of the practitioner. The adjustment control may consist of a pressure/friction twist knob that screws against the adjustable portion holding it into place. Other options may include a pin and hole arrangement, where there are holes in the adjustable portion (not shown) that can accept a pin or rod to hold the adjustable portion at a corresponding position. Another alternative may involve a hydraulic lift and lever arrangement such as is used for adjusting the heights of office chairs. Another alternative may involve an adjustable pivot, so the support can turn and twist as the practitioner bends and twists over the procedure table.

As will be discussed further, the apparatus may include one vertical support or two. Similarly, the apparatus may include two horizontal supports extending outwards from the vertical support, or one horizontal support extending outwards from one side of the vertical support. The vertical support may also have or consist of a spring component that can bend and straighten easily as the practitioner moves. In the embodiment of FIG. 1, the horizontal support 24 may consist of one piece of material mounted on the top of the centrally located vertical support. For purposes of discussion here, this arrangement will be referred to as having two horizontal supports.

In addition, the horizontal support 24 may have an optional terminating portion 26. In the embodiment of FIG. 1, the terminating portion consists of a loop at the end of each horizontal support. The loop may support the shoulder portions of the protective wear such that the practitioner would insert his/her arms through the loops. In that example, the loops may only consist of half loops. Alternatively, the loops may be positioned to reside behind the practitioner's shoulders and provide extra support for the protective wear at the arm hole points.

Figure 2:
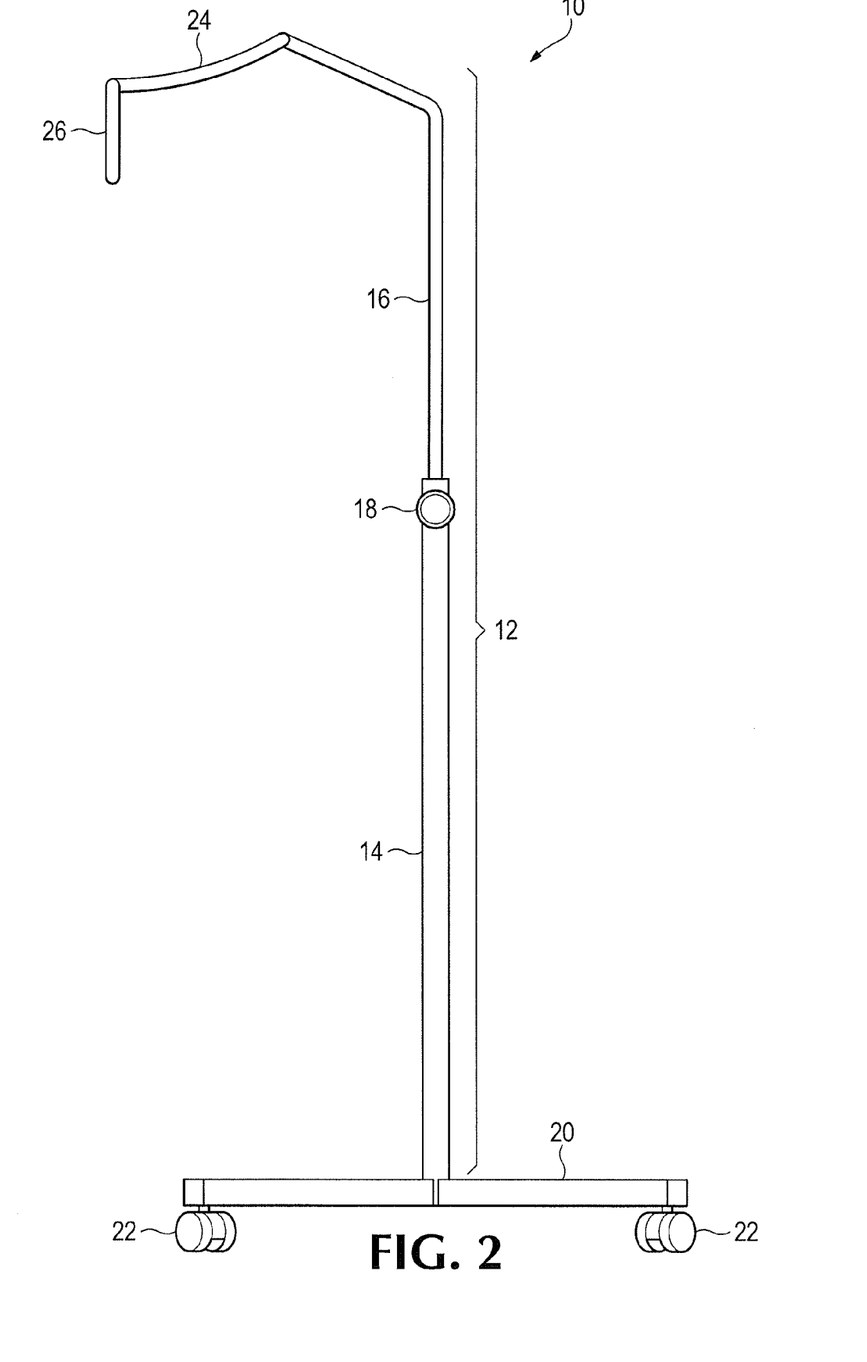
FIG. 2 shows a side view of an embodiment of a support structure for protective wear.
Figure 3:
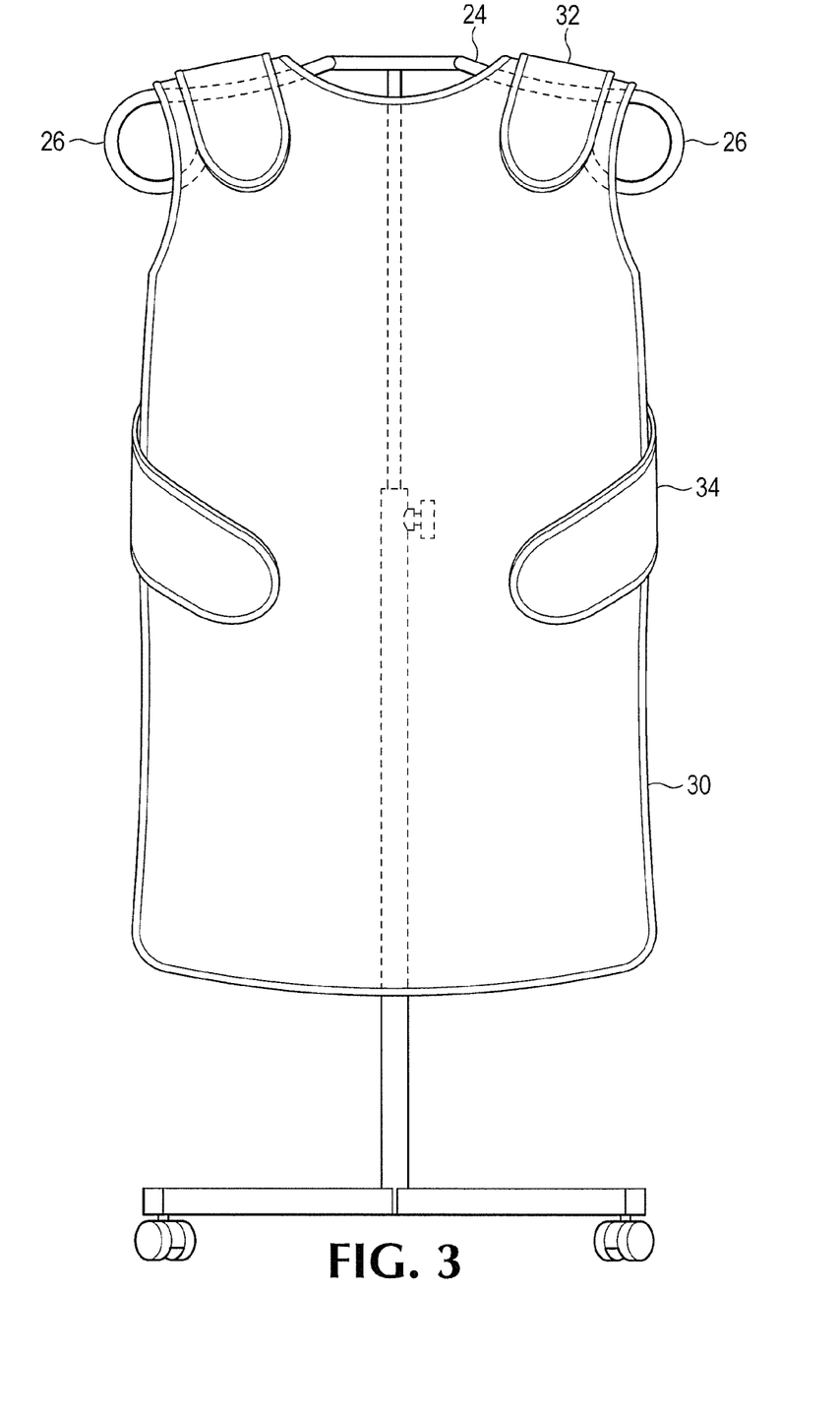
FIG. 3 shows an embodiment of a support structure for protective wear with an example of protective wear.
Figure 4:
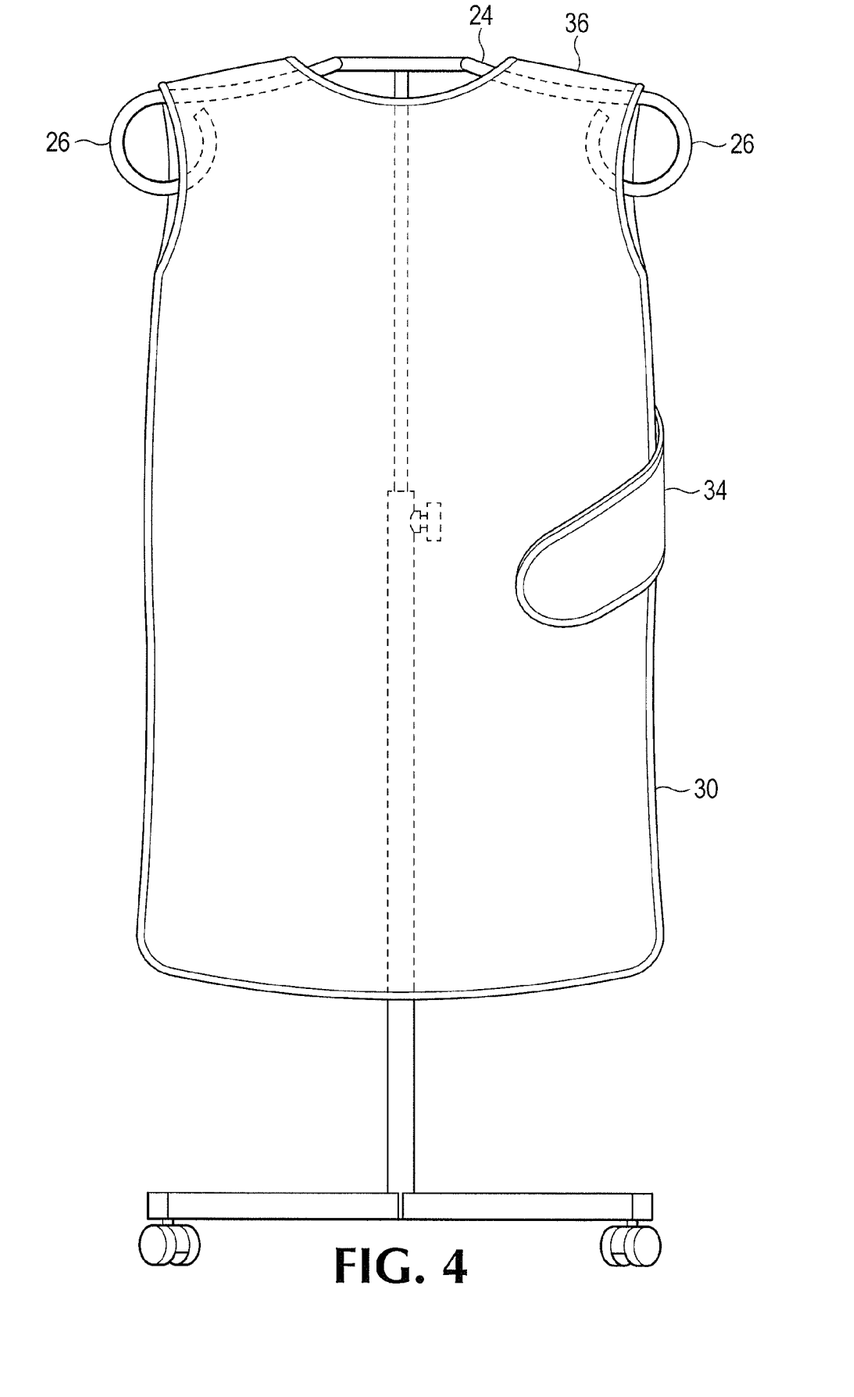
FIG. 4 shows a back view of an embodiment of a support structure for protective wear with an example of protective wear.

FIG. 2 shows a side view of a support apparatus similar to that of FIG. 1. FIGS. 3 and 4 show front and back views of the apparatus of FIG. 1 including an example of a protective wear garment 30. While not shown, the user would be wearing the garment and the support apparatus would carry the load of the garment while still allowing the user to move around the operating room as needed. In FIG. 3, the particular embodiment of the protective wear has a shoulder attachment 32 and a waist attachment 34 that allow the user to fasten the protective wear to his/her body. The back shoulder portion 36 in FIG. 4 may be a portion of the protective wear that requires additional support, as mentioned above.

Figure 5:
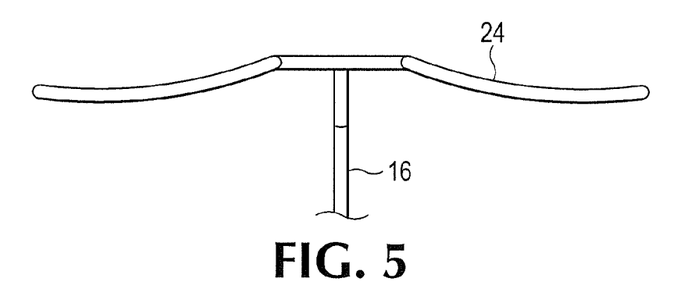
FIGS. 5 and 6 show embodiments of horizontal supports for a support structure.
Figure 6:
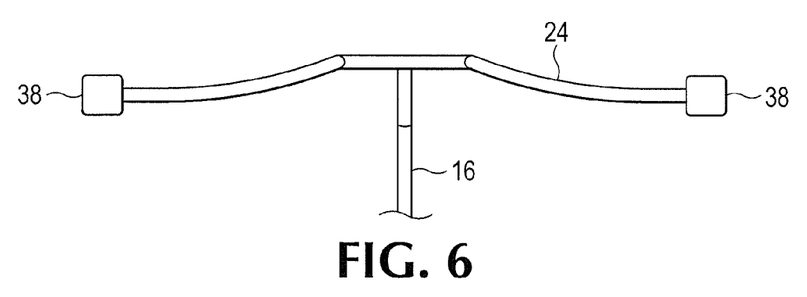

FIGS. 5 and 6 show examples of alternative embodiments of the horizontal support(s) 24. In FIG. 5, the horizontal support consists of arms or branches similar to a hanger. FIG. 6 shows a terminating portion 38 of the support that may extend forward coming out of the page to lend additional support to the shoulder portion of the protective wear. These merely provide examples of possible horizontal supports without any intention of limiting any particular aspect of the claims. Any horizontal support capable of supporting the protective wear would fall within the scope of this invention as set out in the below claims.

Figure 7:
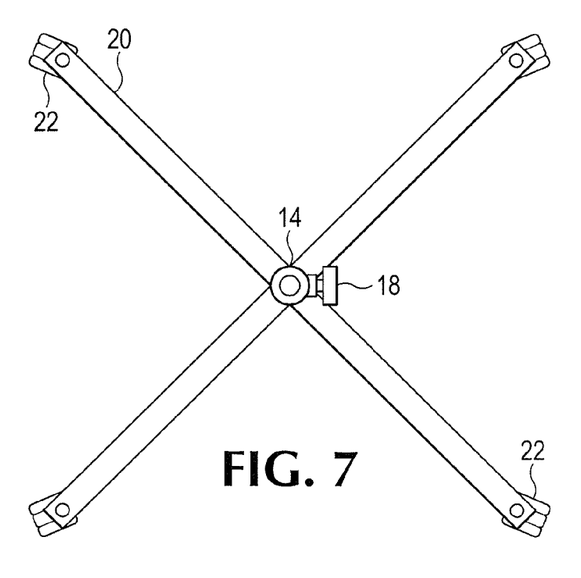
FIGS. 7-9 show embodiments of a base for a support structure.
Figure 8:
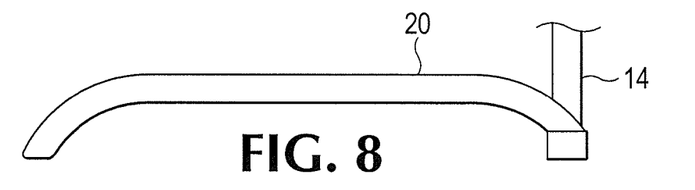
Figure 9:
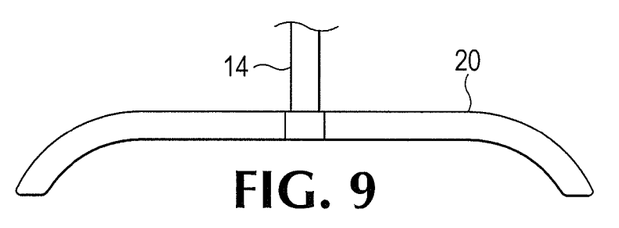

Similarly, FIGS. 7-10 show examples of different configurations of the base. In FIG. 7, a top view of the base 20 is shown. In FIG. 7, the base consists of four spokes that radiate outward from the centrally located vertical support, viewed in this orientation as the outer circumference of the fixed lower portion 14. FIG. 8 shows a base 20 extending outwards from a vertical support on only one side of the support 14. FIG. 9 shows a base 20 having two spokes extending outwards from a centrally located vertical support 14. Again, these are merely examples of the types of variations this structure could include and no limitation to any particular structure is intended nor should any be assumed.

The base would have at least one 'foot' that actually rests upon the ground. In the examples here, the feet consist of wheels to allow the apparatus to move around with the practitioner. Other types of feet may include 'sliders' such as hard plastic discs with a slippery surface that allow users to move pieces of furniture.

Figure 10:
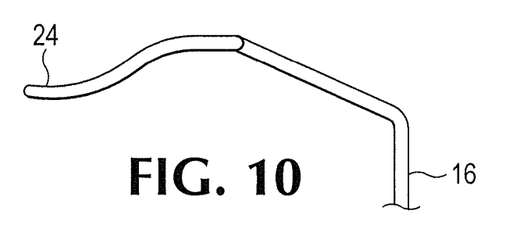
FIGS. 10-11 show embodiments of horizontal supports for a support structure.
Figure 11:
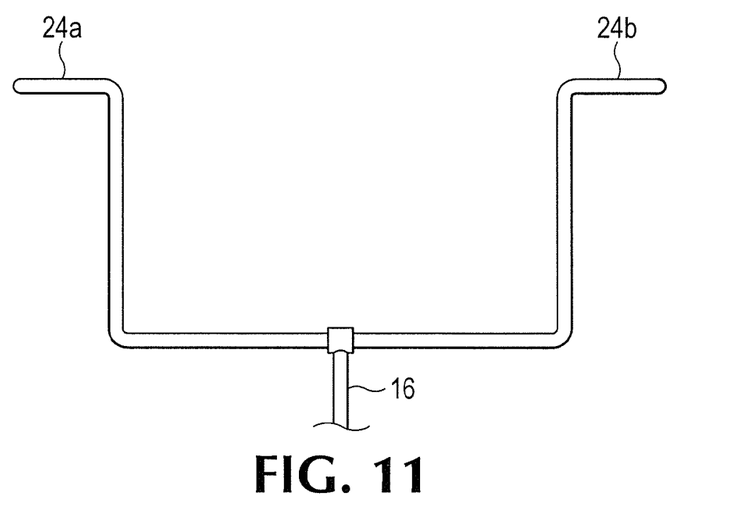

FIGS. 10 and 11 show alternatives for the horizontal supports. FIG. 11 shows a horizontal support in which the ends of the support 24 extend in a manner that would have them extending across the shoulders of the practitioner from the practitioner's back. This may be limited by the shape and fit of the protective wear garment.

FIG. 11 shows a different arrangement than a horizontal support extending only outwards from the vertical support. As can be seen, the horizontal support 24 has two portions 24a and 24b, each of which extend outwards from the vertical support adjustable portion 16 and then upwards along what would be either side of the practitioner's back with the final portion inserting through the back side of the protective wear, near the practitioner's neck and into the shoulders of the protective wear.

Figure 12:
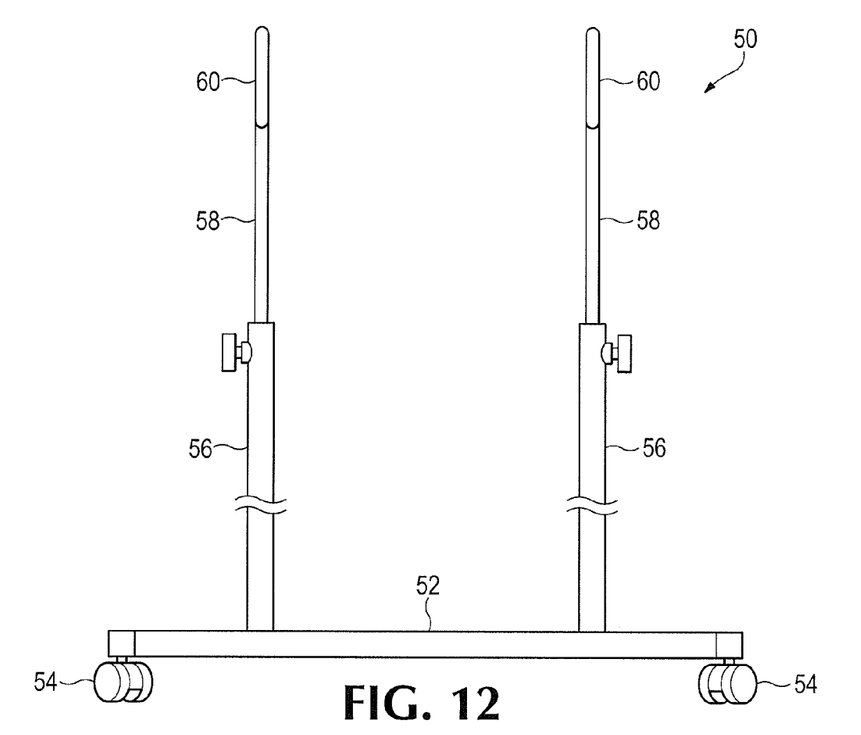
FIGS. 12 and 13 show views of embodiments of a support structure.
Figure 13:
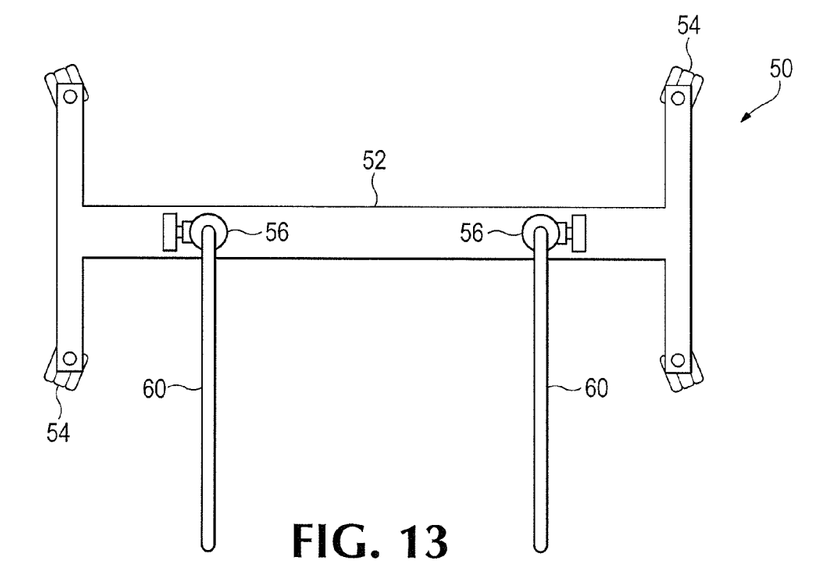

FIGS. 12 and 13 show an alternative support structure 50, having two vertical supports rather than one. In this example, the base 52 may be slightly wider than the base 20 of FIG. 1 to accommodate both supports. This particular base also includes wheels 54. Each vertical support would have a lower fixed portion 56, an upper adjustable portion 58, and a horizontal support 60. As can be seen in the top view of FIG. 13, the horizontal support may extend towards the user and be insertable into the shoulder openings of the protective wear.

One must note that while the above examples assume that the support structure stands behind the practitioner, the support structure could stand in front of the practitioner as well. As another alternative, the support structure could mount onto the procedure table 70 by a clamp or other device 72, as shown in FIG. 14.

Figures 14, 15:
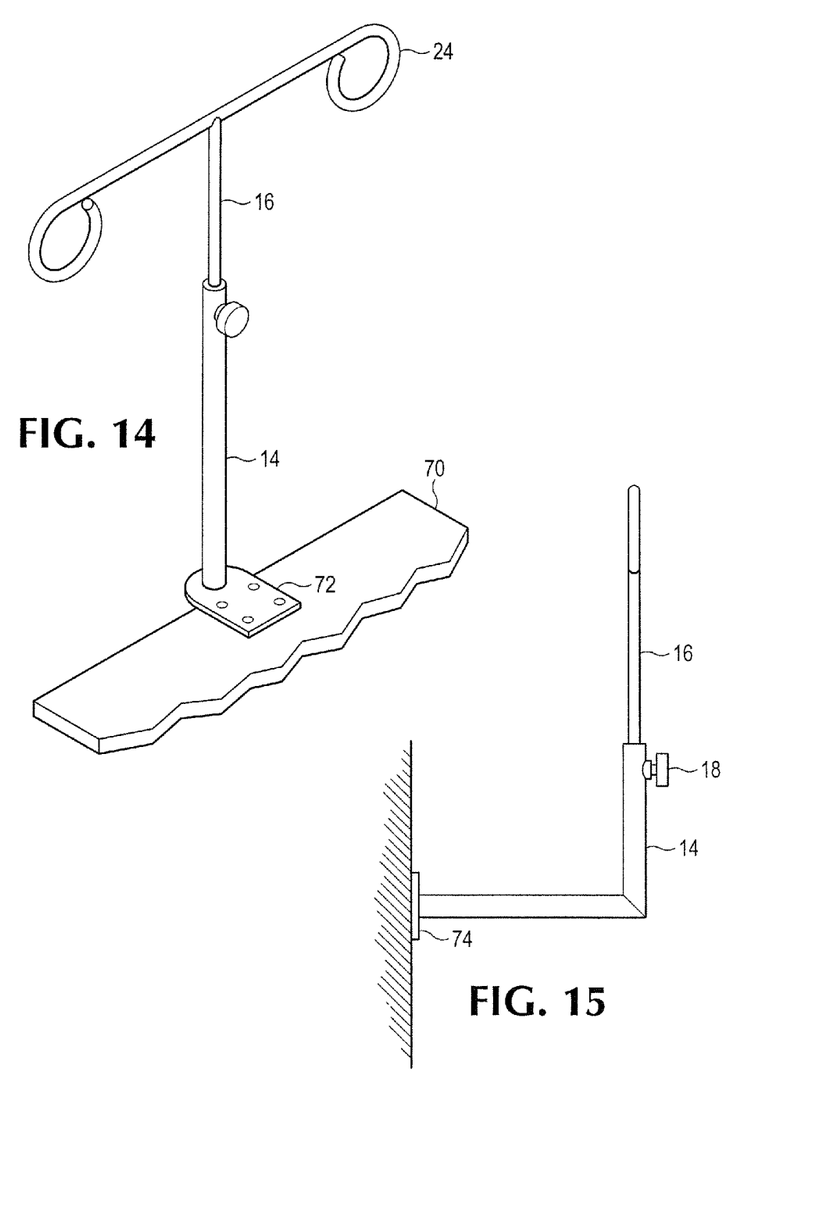
FIG. 14 shows an embodiment of a table mounted support structure.
FIG. 15 shows an embodiment of a wall-mounted support structure.
Figure 16:
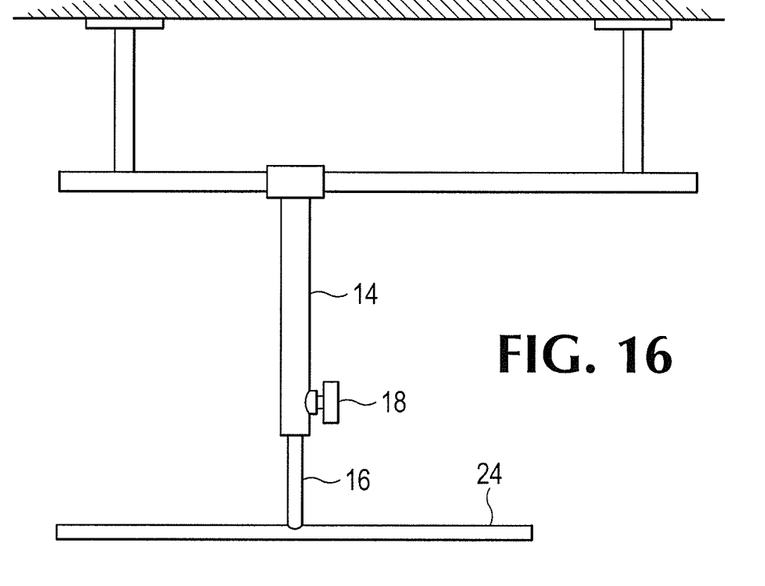
FIG. 16 shows an embodiment of a ceiling-mounted support structure.
Figure 17:
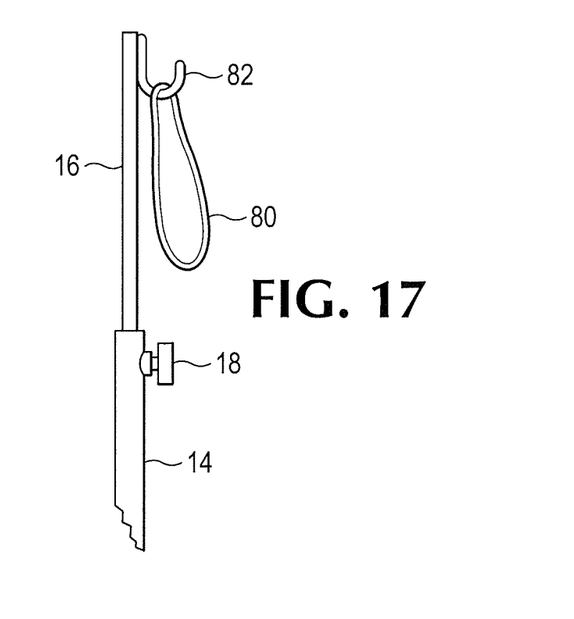
FIG. 17 shows an embodiment of a cable horizontal support.

FIGS. 15-17 show other alternatives for support structures. FIG. 15 shows a support pole coming from a wall behind the practitioner to support the protective wear. The support pole may include a hinge 74 that allows the pole to move laterally relative to the operating table.

FIG. 16 shows a support from the ceiling. This may involve a suspended track within which the pole moves, or could involve a less rigid support such as a cable and hook arrangement.

FIG. 17 integrates cables as well. In FIG. 17, the support pole does not have a support bracket 24, it has a cable 80 that can be looped through the shoulder openings. The cable then attaches to the support pole such as by hook 82 to lift the weight of the protective wear off of the practitioner. The cable may also exist separately from the support, rather than being attached to it, and the support may have a hook or other fitting to which the cable attaches.

Figure 18:
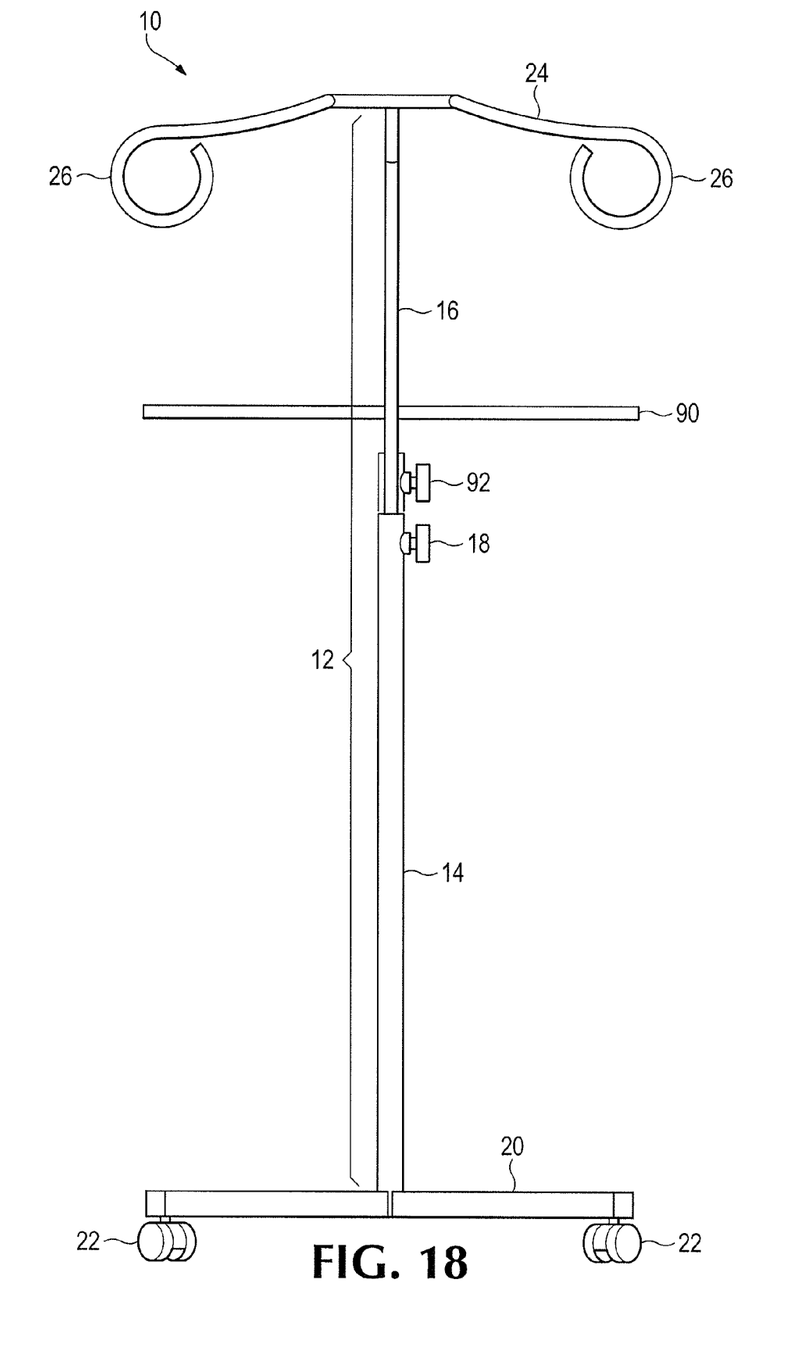
FIG. 18 shows an embodiment of a support structure for upper and lower body protective wear.

In yet another alternative, the protective wear discussed up to this point has included only the full apron. However, other types of protective wear exists, including vests or upper body protective wear only, kilts or skirts only, or sets that combine the two. The support structure could include a lower support structure to support just the kilt, skirt or other piece of lower body protective wear, or support the kilt from the lower support and the vest from the upper support, as shown in FIG. 18. The lower support 90 may have its own adjustment mechanism 92 to allow for different heights for both the lower and upper body pieces of protective wear.

The above discussion includes many examples and embodiments in different combinations. While not explicitly shown here, any variation on any portion of the support structure is usable with any variation on any other portion or portions of the structure. No limitation to any particular structure or example is intended.

The use of this structure allows the practitioner to remain fully protected by full-weight protective wear, but not to have to bear its weight. The structure could be manufactured out of materials that can be disinfected and/or decontaminated, such as stainless steel, to allow full use in operating rooms. Similarly, while use in an operating room is discussed above, this structure may be used in any environment in which protective garments are worn against radiation. The radiation may be x-ray or other radiation.

Thus, although there has been described to this point a particular embodiment for a support structure for protective wear, it is not intended that such specific references be considered as limitations upon the scope of this invention except in-so-far as set forth in the following claims.

What is claimed is:

1. A protective wear support system, comprising:
   a protective garment having shoulder attachments to allow a user to fasten the protective garment over the shoulders of a user; and
   a support apparatus, comprising:
      a base having at least one portion positioned to rest on a solid surface,
      only one vertical support extending upwards from the base, the vertical support having a lower fixed portion and an upper adjustable portion including a first portion of the upper adjustable portion extending along a longitudinal axis of the support apparatus and a second portion of the upper adjustable portion extending along an axis angled with respect to the longitudinal axis; and
      two horizontal supports directly connected to and extending horizontally outwards in opposite directions from the top of the second portion of the upper adjustable portion of the only one vertical support, a first portion of each of the two horizontal supports extends downwardly and is concavely curved and a second portion of each of the two horizontal supports includes a terminating portion extending along an axis parallel to the longitudinal axis, the terminating portion including a loop, wherein the horizontal supports are configured to support a top portion of the protective garment while the protective garment is worn by the user.

2. The protective wear support system of claim 1, the support apparatus further comprising an adjustment control to raise and lower the upper adjustable portion relative to the lower fixed portion.

3. The protective wear support system of claim 2, wherein the adjustment control comprises one of a friction knob, a pin and hole arrangement, a pivot, or a hydraulic lever.

4. The protective wear support system of claim 1, wherein the base comprises one of a wheel or a slider.

5. The protective wear support system of claim 1, wherein the two horizontal supports comprise horizontal supports extending outwards on opposite sides of the vertical support.

6. The protective wear support system of claim 1, the support apparatus further comprising a third horizontal support positioned to support lower body protective wear.

7. The protective wear support system of claim 1, wherein the base portion configured to rest on a solid surface comprises the base portion configured to rest on one of a table or a floor.

8. The protective wear support system of claim 1, wherein the terminating portions are positioned to reside behind shoulders of a user when the user is wearing the protective garment.

* * * * *